United States Patent
Way (12) 
(10) Patent No.: US 6,465,192 B2
(45) Date of Patent: Oct. 15, 2002

(54) COMPOUNDS AND METHODS FOR THE INHIBITION OF PROTEIN-PROTEIN INTERACTIONS

(75) Inventor: Jeffrey C. Way, 71 Walker St., Cambridge, MA (US) 02138

(73) Assignee: Jeffrey C. Way, Canbridge, MA (US)

( * ) Notice: Subject to any disclaimer, the term of this patent is extended or adjusted under 35 U.S.C. 154(b) by 0 days.

(21) Appl. No.: 09/208,665

(22) Filed: Dec. 10, 1998

(65) Prior Publication Data

US 2002/0031780 A1 Mar. 14, 2002

Related U.S. Application Data

(60) Provisional application No. 60/103,517, filed on Oct. 8, 1998, and provisional application No. 60/069,548, filed on Dec. 12, 1997.

(51) Int. Cl.$^7$ .......................... G01N 33/53; C07K 1/100; C07K 14/00; C07K 17/00; C12P 21/08

(52) U.S. Cl. ...................... 435/7.1; 435/6; 435/DIG. 2; 435/DIG. 46; 530/350; 530/387.3

(58) Field of Search ........................ 435/7.1, 6, DIG. 2, 435/DIG. 46; 530/350, 387.3

(56) References Cited

U.S. PATENT DOCUMENTS

| | | | |
|---|---|---|---|
| 5,372,933 A | 12/1994 | Zammarron et al. | 435/7.21 |
| 5,552,534 A | 9/1996 | Hirschmann et al. | 536/17.4 |
| 5,571,681 A | 11/1996 | Janda | |
| 5,639,603 A | 6/1997 | Dower et al. | |
| 5,658,727 A | 8/1997 | Barbas et al. | |

FOREIGN PATENT DOCUMENTS

WO 9604557 * 2/1996

OTHER PUBLICATIONS

Delforge et al., "Identification of Lysine 74 in the Pyruvate Binding Site of Alanine Dehydrogenase from *Bacillus subtilis*," *J. Biol. Chem.* 272:2276–2284 (1997).
Erlanson et al., "Site–directed Ligand Discovery," *Proc. Nat. Acad. Sci.* 97:9367–9372 (2000).
Fersht, "Structure and Mechanism in Protein Science," 2$^{nd}$ Edition, W. H. Freeman & Co., New York, Ch. 9 248–263 (1985).
Fersht, "Structure and Mechanism in Protein Science: A Guide to Enzyme Catalysis and Protein Folding," 3$^{rd}$ Edition, W. H. Freeman & Co., New York, Ch. 9 273–288 (1999).
McCray and Weil, "Inactivation of Interferons: Halomethyl Ketone Derivatives of Phenylalanine as Affinity Labels," *Proc. Nat. Acad. Sci.* 79:4829–4833 (1982).
Plummer et al., "Design Synthesis and Cocrystal Structure of a Nonpeptide Src SH2 Domain Ligand," *J. Med. Chem.* 40:3719–3725 (1997).

Takasaki et al., "Structure–based Design and Characterization of Exocyclic Peptidomimetics that Inhibit TNFα Binding to its Receptor," *Nature Biotechnology* 15:1266–1270 (1997).
Tilley et al., "Identification of a Small Molecule Inhibitor of the IL–2/IL–2Rα Receptor Interaction which Binds to IL–2," *J. Am. Chem. Soc.* 119:7589–7590 (1997).
Atlas, et al. "Bromocholchicine As A Label For Tubulin," *Methods in Enzymology*, 46:567–572 (1977).
Atlas, et al. "Affinity Labelling of Receptors," *Methods in Enzymology*, 46:572–590 (1977).
Atlas, et al. "β–Adrenergic Receptors," *Methods in Enzymology*, 46:591–601 (1977).
Abate et al., "Redox Regulation of Fos and Jun DNA–Binding Activity in Vitro," *Science*, 249:1157–1161 (1990).
Benisek et al., "Attachment of Metal–chelating Functional Groups to Hen Egg White Lysozyme," *The Journal of Biological Chemistry*, 243:4267–4271 (1968).
Bridges et al., "The Acetylation of Hemoglobin by Aspirin in Vitro and in Vivo," *The Journal of Clinical Investigation*, 56:201–207 (1975).
Brown et al., "Rates of Solvolysis of the m– and p–Phenyl–, m– and p–Methylthio–, and m– and p–Trimethylsilyphenyldimethylcarbinyl Chlorides. Steric Inhibition of Resonance as a Factor in Electrophilic Substituent Constants," *Journal of the American Chemical Society*, 80:4964–4968 (1958).
Brown et al., "Rates of Solvolysis of the Halophenyldimethylcarbinyl Chlorides. The Effect of Halogen Substituents upon the Rates of Electrophilic Reactions," *Journal of the American Chemical Society*, 79:1906–1917 (1957).
Corran et al., "The Reaction of Penicillin with Proteins," *Biochem. J.*, 149:357–364 (1975).
Delaney et al., "Alternative Diaspirins for Modification of Hemoglobin and Sickle Hemoglobin," *Archives of Biochemistry and Biophysics*, 228:627–638 (1984).
Devos et al., "Covalent modification of the interleukin–5 receptor by isothiazolines leads to inhibition of the binding of interleukin–5," *Eur. J. Biochem.*, 225:635–640 (1994).
Fersht, "Chemical Catalysis,"*In Enzyme Structure and Mechanism*, 2nd Ed W.H. Freeman and Company,New York, pp 57–59.

(List continued on next page.)

*Primary Examiner*—Jyothsna Venkat
(74) *Attorney, Agent, or Firm*—Clark & Elbing LLP (57) ABSTRACT

Compounds having molecular weights of less than 1500 daltons that non-covalently interact with target proteins and covalently bond to target proteins at amino acid side chains that are not part of enzyme active sites, in which covalently bound portions of the compounds sterically block the binding of the target proteins to other proteins, are disclosed. The compounds react with forward reaction rates at least 100 times faster than the forward reaction rates at which the compounds bond to the side chains of the corresponding free amino acids under physiological conditions. Compositions including these compounds and methods for preparing these compounds are also disclosed.

11 Claims, 4 Drawing Sheets

OTHER PUBLICATIONS

Friedman et al., "Application of a Hammett–Taft Relation to Kinetics of Alkylation of Amino Acid and Peptide Model Compounds with Acrylonitrile," *Journal of the American Chemical Society*, 86:3735–3741 (1964).

Friedman et al., "Additive Linear Free–Energy Relationships in Reaction Kinetics of Amino Groups with $\alpha,\beta$–Unsaturated Compounds," *J. Org. Chem.* 31:2888–2894 (1966).

Friedman et al., "Relative Nucleophilic Reactivities of Amino Groups and Mercaptide Ions in Addition Reactions with $\alpha,\beta$–Unsaturated Compounds," *Journal of the American Chemical Society*, 87: 3672–3681 (1965).

Friedman, "Solvent Effects in Reactions of Amino Groups in Amino Acids, Peptides, and Proteins with $\alpha,\beta$–Unsaturated Compounds," *Journal of the American Chemical Society*, 89: 4709–4713 (1967).

Glazer, "The Chemical Modification of Proteins by Group–Specific and Site–Specific Reagents," *The Proteins, Hans Neurath and Robert L. Hill* 3$^{rd}$ Ed., vol. II, Academic Press, NY, NY pp. 1–103 (1976).

Gu et al., "Absence of Monocyte Chemoattractant Protein–1 Reduces Atherosclerosis in Low Density Lipoprotein Receptor–Deficient Mice," *Molecular Cell*, 2:275–281 (1998).

Hajduk et al., "Discovering High–Affinity Ligands for Proteins," *Science*, 278:497–499 (1997).

Handel et al., "Heteronuclear ($^1$H, $^{13}$C, $^{15}$N) NMR Assignments and Solution Structure of the Monocyte Chemoattractant Protein–1 (MCP–1) Dimer" *Biochemistry* 35:6569–6584 (1996).

Harding, "Nonenzymatic Covalent Posttranslational Modification of Proteins In Vivo," *Advances in Protein Chemistry*, 37:247–333 (1985).

Heinrikson et al., "The Reactivities of the Histidine Residues at the Active Site of Ribonuclease toward the Halo Acids of Different Structures," *The Journal of Biological Chemistry*, 240:2921–2934 (1965).

Hine et al., "The Effect of Halogen Atoms on the Reactivity of Other Halogen Atoms in the Same Molecule. III. The $S_N2$ Reactivity of Ethylene Halides," *Journal of the American Chemical Society*, 75:3964–3966 (1953).

Hine et al., "The Effect of Halogen Atoms on the Reactivity of Other Halogen Atoms in the Same Molecule. V. The $S_N2$ Reactivity of Methylene Halides," *Journal of the American Chemical Society*, 77:3886–3889 (1955).

Kalgutkar et al., "Aspirin–like Molecules that Covalently Inactivate Cyclooxygenase–2," *Science*, 280:1268–1270 (1998).

Klotz et al., "Rational Approaches to Chemotherapy: Antisickling Agents," *Science*, 213:724–731 (1981).

Klotz et al., "Specific Chemical Modifications in the $\beta$–Cleft Site of Hemoglobin," *The Journal of Biological Chemistry*, 260:16215–16223 (1985).

Li et al., "A computer screening approach to immunoglobulin superfamily structures and interactions: Discovery of small non–peptidic CD4 inhibitors as novel immunotherapeutics," *Proc. Natl. Acad. Sci. USA* 94:73–78 (1997).

Lowry et al., Mechanism and Theory in Organic Chemistry 3rd Ed. Harper Collins Publishers, pp 143–400.

MacQuarrie et al., "Mechanism of Alkylation of Rabbit Muscle Glyceraldehyde 3–Phosphate Dehydrogenase," *Biochemistry*, 10:2456–2466 (1971).

Martin et al., "Measuring Diversity: Experimental Design of Combinatorial Libraries for Drug Discovery," *J. Med. Chem.* 38:1431–1436 (1995).

Massil et al., "Acylation of Hemoglobin by Aspirin–Like Diacyl Esters," *Journal of Pharmaceutical Sciences*, 73:1013–1014 (1984).

Maugh, "Sickle Cell (II) Many Agents Near Trials" *Science* 211:468–470 (1981).

Newman, "Irreversible Ligands for Drug Receptor Characterization" *Annual Reports in Medicinal Chemistry* 25:271–280 (1998).

Okamoto et al., "Rates for Solvolysis of Phenyldimethylcarbinyl Chlorides Containing Meta Directing Substituents," *Journal of the American Chemical Society*, 80:4969–4987 (1958).

Parameswaran et al., "O–Carbamoylsalicylates: Agents for Modification of Hemoglobins," *J. Med. Chem.*, 30:936–939 (1987).

Pinckard, "In vitro Acetylation of Plasma Proteins, Enzymes and DNA by Aspirin," *Nature*, 219:68–69 (1968).

Plapp et al., "Activity of Bovine Pancreatic Deoxyribonuclease A with Modified Amino Groups," *The Journal of Biological Chemistry*, 246:939–945 (1971).

Plummer et al., "Design, Synthesis, and Cocrystal Structure of a Nonpeptide Src SH2 Domain Ligand," *J. Med. Chem.*, 40:3719–3725 (1997).

Popov et al., "Critical role of reverse transcriptase in the inhibitory mechanism of CNI–H0294 on HIV–1 nuclear translocation," *Proc. Natl. Acad. Sci. USA*, 93:11859–11864 (1996).

Priestle et al., "Crystallographic refinement of interleukin 1$\beta$ at 2.0 Å resolution," *Proc. Natl. Acad. Sci. USA*, 86:9667–9671 (1989).

Rhodes et al., "Therapeutic potentiation of the immune system by costimulatory Schiff–base–forming drugs," *Nature*, 377:71–75 (1995).

Schneider et al., "Studies on the Direct Neutral Penicilloylation of Functional Groups Occurring on Proteins," *Biochim. Biophys. Acta*, 168:27–35 (1968).

Schneider et al., "A New Chemical Aspect of Penicillin Allergy: The Direct Reaction of Penicillin with $\epsilon$–Amino–Groups," *Nature*, 208:57–59 (1965).

Schreuder et al., "A New Cytokine–Receptor Binding Mode Revealed by the Crystal Structure of the IL–1 Receptor with an Antagonist," *Nature*, 386:194–200 (1997).

Shuker et al., "Discovering High–Affinity Ligands for Proteins: SAR by NMR,"*Science*, 274:1531–1534 (1996).

Singer, "Covalent Labeling of Active Sites" *Advances in Protein Chemistry*, C.B. Anfinsen, M.L. Auson, J.T. Edsall, F.M. Richards, Eds., Academic Press, NY, NY 22:1–55 (1967).

Singh et al., "Structure–Based Design of a Potent, Selective, and Irreversible Inhibitor of the Catalytic Domain of the erbB Receptor Subfamily of Protein Tyrosine Kinases," *J. Med. Chem.*, 40:1130–1135 (1997).

Vigers et al., "Crystal Structure of the Type–I Interleukin–1 Receptor Complexes with Interleukin–1$\beta$," *Nature* 386:190–194 (1997).

Wallenfels et al., "Stereospecific Alkylation with Asymmetric Reagents," *European J. Biochem.*, 3:267–275 (1968).

Wood et al., "Structural Specificities in Acylation of Hemoglobin and Sickle Hemoglobin by Diaspirins," *The Journal of Biological Chemistry*, 256:7046–7052 (1981).

Wu et al., "Discovery of TBC11251, a Potent, Long Acting, Orally Active Endothelin Receptor–A Selective Antagonist," *J. Med. Chem.*, 40:1690–1697 (1997).

Wu et al., "Structure–Activity Relationships of $N^2$–Aryl–3–(isoxazolysulfamoyl)–2–thiophenecarboxamides as Selective Endothelin Receptor–A Antagonists," *J. Med. Chem.*, 40:1682–1689 (1997).

Zaugg et al, "Modification of Hemoglobin with Analogs of Aspirin," *J. Biol. Chem.* 255:2816–2821 (1980).

Zutshi et al. "Inhibiting the assembly of protein–protein interfaces" *Current Opinion in Chemical Biology* 2:62–66 (1998).

\* cited by examiner

COMPOUNDS AND METHODS FOR THE INHIBITION OF PROTEIN-PROTEIN INTERACTIONS

This application claims priority from U.S. Ser. No. 60/103,517, filed Oct. 8, 1998 and U.S. Ser. No. 60/069,548, filed Dec. 12, 1997.

BACKGROUND OF THE INVENTION

The invention relates to compounds, compositions, and methods for blocking protein-protein interactions.

Figure 1A:
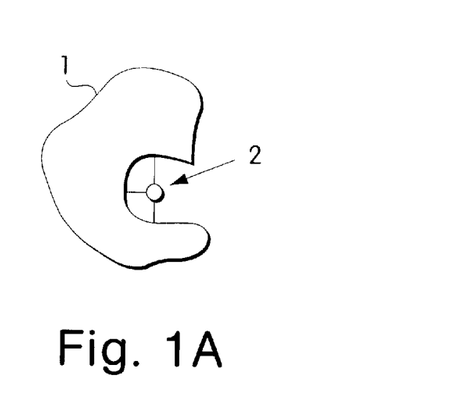
FIG. 1A is a schematic representation of an enzyme bound to its substrate.
Figure 1B:
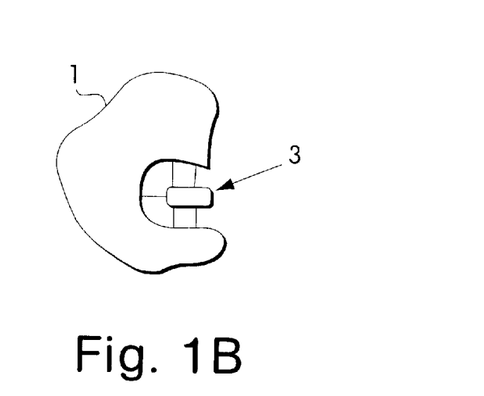
FIG. 1B is a schematic representation of an enzyme bound to an enzyme inhibitor.

Many pharmaceutical drugs act by blocking the binding of an enzyme to its substrate. In order for these drugs to block this interaction effectively, they must bind to the target enzymes more tightly than the substrate binds. Binding strengths are determined in part by the number of favorable contacts between the compounds. Since most enzyme substrates are small molecules, small molecule drugs can be engineered to make as many (or, if desired, more) contacts with the enzyme than does the substrate, facilitating tight enzyme interactions. As an illustration, FIG. 1A shows an enzyme 1 bound to its substrate 2. FIG. 1B shows the enzyme 1 bound to a small molecule drug 3. In addition, because enzymes work by lowering the energy of the transition state between substrate and product, the enzyme binds to especially tightly to transition state analogues. Drugs that resemble the transition state can bind more tightly to an enzyme than does the normal substrate, again affording an opportunity for antagonist-type drug design.

Figure 1C:
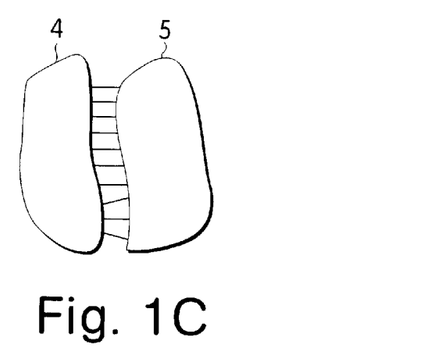
FIG. 1C is a schematic representation of two interacting proteins.

In contrast, it is generally more difficult to engineer small molecule compounds that block the interaction of a target protein with another protein, because interacting proteins usually contact each other over large surface areas and make many favorable contacts. It is therefore difficult for a small molecule to have a greater number of favorable contacts with a protein than does another protein. As an illustration, FIG. 1C shows two such interacting proteins, 4 and 5, and indicates the large number of favorable contacts between these proteins. In addition, interacting proteins do not possess transition states analogous to those exhibited by substrates and their products. Thus, there is no specialized conformation that a drug can mimic to bind more effectively to a target protein.

There are many instances in which it is therapeutically useful to block the interaction of a target protein with another protein. Examples of biological events that involve protein-protein interactions include signal transduction, transcription, protein ligand-receptor interactions, and protein assembly.

The ability to block these processes specifically facilitates the development of therapies for diseases that are currently difficult to treat. Accordingly, compounds that block interactions such as those described above represent potentially useful drugs for treating, preventing, or reducing the severity of certain diseases or their symptoms. For example, viral infections (such as herpes, hepatitis C, HIV, and influenza infections) could be treated with compounds that block the assembly of viral proteins, or with compounds that prevent the ligand-receptor interaction of a virus attaching to a host cell.

SUMMARY OF THE INVENTION

The invention features a compound having a molecular weight of less than 1500 daltons that non-covalently interacts with, and covalently bonds to, a target protein at an amino acid side chain that is not part of an enzyme active site; a covalently bound portion of the compound sterically blocks the binding of the target protein to a second protein. The compound bonds to the target protein with a forward reaction rate that is at least 100 times faster than the forward reaction rate at which the compound bonds to the side chain of the corresponding free amino acid under physiological conditions. The compound may bond in such a way that essentially all, most, or only a small portion, of the compound remains covalently attached to the target protein; another portion of the compound may serve as a leaving group. For example, in some instances, only an acyl group, preferably an acetyl group, remains attached to the target protein.

A preferred compound bonds to the target protein with a forward reaction rate that is at least 1000 times faster than the forward reaction rate at which the compound bonds to the side chain of the free amino acid under physiological conditions, and more preferably bonds with a rate 10,000 times, or 100,000 times faster. The compound is preferably a synthetic compound.

In addition, a preferred compound has a covalent bonding rate constant with the side chain of the free amino acid of less than $10^{-5}$/M/sec at room temperature under physiological conditions, and more preferably has a rate constant of less than $10^{-6}$/M/sec, or $10^{-7}$/M/sec at room temperature under physiological conditions.

The non-specific covalent bonding rate constant for penicillin to form stable bonds with amino acid side chains, such as those of serine and lysine, is about $8 \times 10^{-6}$/M/sec. Because penicillin is a useful drug whose side effects, which are results of its reactivity, are considered to be acceptable, it is expected that the side effects resulting from the non-specific reactivity of drugs with similar or smaller covalent bonding rate constants will also be acceptable.

A preferred compound also includes a Specificity Group whose removal results in the bonding reaction rate with the side chain of the corresponding free amino acid being substantially unchanged, and the bonding reaction rate with the target protein being reduced to a rate that is substantially similar to the bonding reaction rate with the side chain of the free amino acid; the compound also includes a Bonding Group that forms the covalent bond with the target protein. In this compound, modification of the Specificity Group does not substantially alter the bonding reactivity of the Bonding Group. In such preferred compounds, the Bonding Group and Specificity Group are connected by appropriate linkers, so that, for example, electronic effects are not transmitted from the Specificity Group to the Bonding Group. An example of an appropriate linker is an alkyl chain having 2–12 carbon atoms.

Preferred target proteins include kinases, viral coat proteins, STAT proteins, oncogenes, transcription factors, and extracellular protein ligands, protein domains, and their receptors. More specifically, preferred target proteins include MCP-1, Fos, and IL-1 beta. In a preferred compound, the Bonding Group forms a covalent bond with the side chain of the amino acid of the target protein as a result of the intrinsic reactivity of the Bonding Group.

The purpose of the Specificity Group is to direct the compound to a particular protein target and to position the Bonding Group near an amino acid side chain on the target protein; the Bonding Group will therefore have a high effective concentration, relative to the amino acid side chain, and will react with the side chain. An initial Specificity Group may be obtained by screening conventional chemical compound libraries for compounds that non-covalently interact with the target protein. Alternatively, the initial Specificity Group could be obtained by rational drug design, or by using a peptide that is known to bind to the target protein.

For comparison purposes, the side chain of the free amino acid that corresponds to the amino acid that forms a covalent bond to the B group is used, rather than a side chain on a non-target protein. The side chain of the corresponding free amino acid can always be clearly defined; in addition, it will not be subject to environmental influences, such as steric factors, that may vary from one non-target protein to the next.

It is useful, during the improvement of Bifunctional Blockers that is described in detail below, for the Bonding Group and Specificity Group to be connected so that modification of one Group has little effect on the other. In brief, improvement of Bifunctional Blockers is accomplished by systematically improving the Specificity Group and weakening the reactivity of the Bonding Group. There is an extensive body of knowledge, well known to those skilled in the art of organic chemistry, that predicts the relative reactivity of possible Bonding Groups. This knowledge can be used to systematically alter and weaken a Bonding Group during the course of improvement of a Bifunctional Blocker. However, if the Specificity Group is connected to the Bonding Group in such a way that the Specificity Group's composition influences the Bonding Group's reactivity, then it will be difficult to systematically weaken the reactivity of the Bonding Group. It is therefore preferable to connect these Groups so that they do not influence each other.

The invention also features a compound having a molecular weight of less than 1500 daltons that covalently bonds to an amino acid side chain of a target protein that is not an enzyme; a covalently bound portion of the compound sterically blocks the binding of the target protein to a second protein. The compound bonds to the target protein with a forward reaction rate that is at least 100 times faster than the forward reaction rate at which the compound bonds to the side chain of the corresponding free amino acid under physiological conditions. A preferred compound bonds to the target protein with a forward reaction rate that is at least 1000 times faster than the forward reaction rate at which the compound bonds to the side chain of the free amino acid under physiological conditions, and more preferably bonds with a rate 10,000 times, or 100,000 times faster.

In this case, a preferred compound also has a covalent bonding rate constant with the side chain of the free amino acid of less than $10^{-5}$/M/sec at room temperature under physiological conditions, and more preferably has a rate constant of less than $10^{-6}$/M/sec, or $10^{-7}$/M/sec at room temperature under physiological conditions. A preferred compound is one that is prepared synthetically.

In addition, a preferred compound includes a Specificity Group whose removal results in the bonding reaction rate with the side chain of the free amino acid being substantially unchanged, and the bonding reaction rate with the target protein being reduced to a rate that is substantially similar to the bonding reaction rate with the side chain of the free amino acid; the compound also includes a Bonding Group that forms the covalent bond with the target protein. In this compound, modification of the Specificity Group does not substantially alter the bonding reactivity of the Bonding Group. Preferred target proteins include kinases, viral coat proteins, STAT proteins, oncogenes, transcription factors, and extracellular protein ligands, protein domains, and their receptors. More specifically, preferred target proteins include MCP-1, Fos, and IL-1 beta.

The invention also features a substantially pure compound having a molecular weight of less than 1500 daltons that includes a Specificity Group that non-covalently interacts with the surface of a target protein and a Bonding Group that covalently bonds to the target protein. A covalently bound portion of the compound competitively and sterically inhibits the binding of a second protein to the target protein.

The invention further features a combinatorial chemistry library containing at least 25 compounds. Each compound contains the same Bonding Group, which covalently bonds to the side chains of amino acids. The covalent bonding rate constant is between $10^{-3}$/M/sec and $10^{-7}$/M/sec for the reaction of the Bonding Group with the side chain of the free amino acid that reacts most rapidly with the Bonding Group to give a stable product (i.e., a product that has a sufficiently long half-life in physiological conditions to inhibit the target protein usefully). In preferred libraries, each compound also includes a Specificity Group.

The invention further features a pharmaceutical composition including a compound having a molecular weight of less than 1500 daltons; the compound non-covalently interacts with, and covalently bonds to, a target protein at an amino acid side chain that is not part of an enzyme active site. A covalently bound portion of the compound sterically blocks the binding of the target protein to a second protein. The compound bonds to the target protein with a forward reaction rate that is at least 100 times faster than the forward reaction rate at which the compound bonds to the side chain of the corresponding free amino acid under physiological conditions. The pharmaceutical composition also includes a pharmaceutically acceptable carrier. The pharmaceutical compositions of the invention are free of contaminating substances, such as trace organic solvents and synthetic precursors, that would make the composition unacceptable for clinical use.

In a preferred composition, the compound bonds to the target protein with a forward reaction rate that is at least 1000 times faster than the forward reaction rate at which the compound bonds to the side chain of the free amino acid under physiological conditions, and more preferably bonds with a rate 10,000 times, or 100,000 times faster. In another preferred composition, the compound has a covalent bonding rate constant with the side chain of the free amino acid of less than $10^{-5}$/M/sec at room temperature under physiological conditions, and more preferably has a rate constant of less than $10^{-6}$/M/sec, or $10^{-7}$/M/sec at room temperature under physiological conditions.

Another preferred composition includes a compound that includes a Specificity Group whose removal results in the bonding reaction rate with the side chain of the free amino acid being substantially unchanged, and the bonding reaction rate with the target protein being reduced to a rate that is substantially similar to the bonding reaction rate with the side chain of the free amino acid. In this composition, the compound includes a Bonding Group that forms the covalent bond with the target protein. Modification of the Specificity Group does not substantially alter the bonding reactivity of the Bonding Group. Preferred target proteins include kinases, viral coat proteins, STAT proteins, oncogenes, transcription factors, and extracellular protein ligands and their receptors. More specifically, preferred target proteins include MCP-1, Fos, and IL-1 beta. In a preferred composition, the Bonding Group forms a covalent bond with the amino acid side chain of the target protein as a result of the Bonding Group's intrinsic reactivity.

The invention also features a composition containing a compound having a molecular weight of less than 1500 daltons that non-covalently interacts with, and covalently bonds to, a target protein that is not an enzyme; a covalently bound portion of the compound sterically blocks the binding of the target protein to a second protein. The compound bonds to the target protein with a forward reaction rate that is at least 100 times faster than the forward reaction rate at which the compound bonds to the side chain of the corresponding free amino acid under physiological conditions. A preferred composition includes a compound that bonds to the target protein with a forward reaction rate that is at least 1000 times faster than the forward reaction rate at which the compound bonds to the side chain of the free amino acid under physiological conditions, and more preferably bonds with a rate 10,000 times, or 100,000 times faster.

In another preferred composition, the compound has a covalent bonding rate constant with the side chain of the free amino acid of less than $10^{-5}$/M/sec at room temperature under physiological conditions, and more preferably has a rate constant of less than $10^{-6}$/M/sec, or $10^{-7}$/M/sec at room temperature under physiological conditions.

In addition, a preferred composition contains a compound that includes a Specificity Group whose removal results in the bonding reaction rate with the side chain of the corresponding free amino acid being substantially unchanged, and the bonding reaction rate with the target protein being reduced to a rate that is substantially similar to the bonding reaction rate with the side chain of the free amino acid; this compound also includes a Bonding Group that forms the covalent bond with the target protein. Modification of the Specificity Group does not substantially alter the bonding reactivity of the Bonding Group. Preferred target proteins include kinases, viral coat proteins, STAT proteins, oncogenes, transcription factors, and extracellular protein ligands, protein domains, and their receptors. More specifically, preferred target proteins include MCP-1, Fos, and IL-1 beta.

The invention further features a method of producing a compound that selectively binds to a target protein. The method includes (a) starting with a candidate compound having a molecular weight of less than 1500 daltons and including a first group and a second group, where the second group covalently bonds to an amino acid side chain of the target protein and the first group does not covalently bond to any amino acid side chain, but may non-covalently interact with the target protein; (b) testing the candidate compound for inhibition of the interaction of the target protein and a second protein; (c) testing the candidate compound for binding to a non-target molecule, such as an amino acid or non-target protein; (d) testing the candidate compound for bonding reactivity of the second group with the amino acid side chain of the target protein; (e) altering the first group and selecting for increased selectivity for the target protein, where increased selectivity is indicated by an increase in inhibition of the interaction of the target protein and a second protein, relative to binding to the non-target molecule; (f) altering the second group and selecting for decreased bonding reactivity of the second group with the amino acid side chain of the target protein and with the non-target molecule; and (g) optionally repeating steps (e) and (f), to obtain a compound that has selectivity for the target protein, relative to the non-target molecule, at least 100 times greater than the candidate compound of step (a).

Preferably, the compound selectively binds to the target protein at an amino acid side chain that is not part of an enzyme active site, and also binds to the target protein at a site of protein-protein interaction. In a preferred method, the candidate compound is present in or chosen from a combinatorial chemistry library. In a different preferred method, the compound is designed by principles of rational drug design or with the aid of a computer molecular modeling system. In another preferred method, the first group is a Specificity Group that non-covalently binds to the protein under physiological conditions, the second group is a Bonding Group that forms a covalent bond with the amino acid side chain on the protein, and modification of the Specificity Group does not substantially alter the reactivity of the Bonding Group. In still another preferred method, the candidate compound of step (a) is a compound having a molecular weight of less than 1500 daltons that covalently bonds to a target protein at an amino acid side chain that is not part of an enzyme active site; a covalently bound portion of the compound sterically blocks the binding of the target protein to a second protein. The candidate compound bonds to the target protein with a forward reaction rate that is at least 100 times faster than the forward reaction rate at which the compound bonds to the side chain of the corresponding free amino acid under physiological conditions.

The invention also features a method of producing a compound that selectively binds to a target protein; the method includes (a) starting with a candidate compound having a molecular weight of less than 1500 daltons and including a first group and a second group, where the second group covalently bonds to an amino acid side chain of the target protein and the first group does not covalently bond to any amino acid side chain, but may non-covalently interact with the target protein; (b) testing the candidate compound for inhibition of the interaction of the target protein and a second protein; (c) testing the candidate compound for binding to a non-target molecule, such as an amino acid or non-target protein; (d) testing the candidate compound for bonding reactivity of the second group with the amino acid side chain of the target protein; (e) altering the first group and selecting for increased selectivity for the target protein, where increased selectivity is indicated by an increase in inhibition of the interaction of the target protein and a second protein, relative to binding to the non-target molecule; (f) altering the second group and selecting for decreased bonding reactivity of the second group with the amino acid side chain of the target protein and with the non-target molecule; and (g) optionally repeating steps (e) and (f) to obtain a compound that has a selectivity for the target protein, relative to the non-target molecule, at least 100 times greater than the candidate compound of step (a) and that has a covalent bonding rate with the side chain of the corresponding free amino acid of less than $10^{-5}$/M/sec at room temperature under physiological conditions. Preferably, the compound selectively binds to the target protein at an amino acid side chain that is not part of an enzyme active site, and also binds to the target protein at a site of protein-protein interaction.

The invention also features a method of producing a compound that selectively binds to a target protein including (a) starting with a candidate compound having a molecular weight of less than 1500 daltons and including a first group and a second group, where the second group covalently bonds to an amino acid side chain of the target protein and the first group does not covalently bond to any amino acid side chain, but may non-covalently interact with the target protein; (b) testing the candidate compound for inhibition of the interaction of the target protein and a second protein; (c) testing the candidate compound for binding to a non-target molecule, such as an amino acid or non-target protein; (d) altering the first group and selecting for increased selectivity for the target protein, where increased selectivity is indicated by an increase in inhibition of the interaction of the target protein and a second protein, relative to binding to the non-target molecule; (e) replacing the second group with a group known to be less reactive, altering the first group, and selecting for substantially unchanged or increased inhibition; and (f) optionally repeating steps (d) and (e), to obtain a compound that has a selectivity for the target protein, relative to the non-target molecule, at least 100 times greater than the candidate compound of step (a). Preferably, the compound selectively binds to the target protein at an amino acid side chain that is not part of an enzyme active site, and also binds to the target protein at a site of protein-protein interaction.

Finally, the invention features a method of sterically blocking protein-protein binding. The method includes contacting a target protein with a compound having a molecular weight of less than 1500 daltons, where the compound non-covalently interacts with, and covalently bonds to, the target protein at an amino acid side chain that is not part of an enzyme active site; a covalently bound portion of the compound sterically blocks the binding of the target protein to a second protein. In addition, the compound bonds to the target protein with a forward reaction rate that is at least 100 times faster than the forward reaction rate at which the compound bonds to the side chain of the corresponding free amino acid. The compound has a covalent bonding rate constant with the side chain of the free amino acid of less than $10^{-5}$/M/sec under physiological conditions. Preferred methods include those used for therapeutic or diagnostic purposes. Additional methods include those used for pesticidal or herbicidal purposes.

In preferred methods, the compounds bonds to the target protein with a forward reaction rate 1000 times faster than the rate at which the compound bonds to the side chain of the corresponding free amino acid, or 10,000, or 100,000 times faster. In other preferred methods, the compound has a covalent bonding rate constant with the side chain of the free amino acid of less than $10^{-6}$/M/sec or $10^{-7}$/M/sec under physiological conditions. In addition, in preferred methods, the compound has a Specificity Group and a Bonding Group, and modification of the Specificity Group does not substantially alter the reactivity of the Bonding Group. Preferably, this Bonding Group forms a covalent bond with the side chain of an amino acid of the target protein as a result of the intrinsic reactivity of the Bonding Group.

Preferably, the target protein is not an enzyme and/or the compound is a synthetic compound. Protein-protein binding can be blocked in a mammal, such a human. In preferred instances, the protein-protein binding that is blocked with this method causes a disease.

By a "Specificity Group" or "S group" is meant a moiety that non-covalently interacts with a target protein, causing a Bonding Group to have a high local concentration near an amino acid side chain on the target protein. The formation of a covalent bond between the Bonding Group and the side chain of the amino acid is accelerated.

An important characteristic of the Specificity Group is that its removal results in the bonding reaction rate with the side chain of an amino acid of a target protein being substantially reduced, and the bonding rate with the corresponding free amino acid being substantially unchanged. Alternatively, removal of the Specificity Group from the compound results in the bonding reaction rate with the side chain of the free amino acid being substantially unchanged, and the bonding reaction rate with the amino acid side chain of the target protein being reduced to a rate that is substantially similar to the bonding reaction rate with that of the free amino acid.

By a "Bonding Group" or "B group" is meant a moiety of a compound that forms a covalent bond with an amino acid of a target protein. The Bonding Group does not substantially affect the non-covalent binding affinity of the compound for the target protein.

By "corresponding free amino acid" is meant a free amino acid that is the same amino acid as the amino acid of a target protein that forms a covalent bond with a compound of the invention.

By "protein" is meant a polypeptide having at least 40 amino acids.

By "Bifunctional Blocker" is meant a compound that has an S group and a B group, that reacts selectively with a target protein, and in which a covalently bound portion of the compound sterically hinders the interaction of the target protein with another protein.

By "room temperature" is meant 25° C.±5° C.

By "physiological solution conditions" are meant the conditions, e.g., temperature, pH, and concentration, that are present in the body of the treated organism, such as a human being or other animal, or plant.

By "standard lead-optimization procedures" are meant processes for drug development that begin with the identification of a lead compound in one or more assays for drug activity. The identification is followed by the synthesis of chemical variants of the lead compound, the testing of the variants in the assays, and the selection of compounds with improved activity and selectivity. The steps of synthesis, testing, and selection are often repeated for several cycles.

By "reactive" is meant capable of undergoing covalent bond formation or cleavage on a time scale, at concentrations, and under conditions that are relevant to pharmaceutical development, or under physiological conditions.

By "reactive group" is meant a chemical moiety that is reactive as a result of its intrinsic chemical properties, and that reacts without the action of enzymes, photons, or molecules that are not present under physiological conditions.

By "intrinsic reactivity" is meant the ability to undergo covalent bond formation or cleavage without the action of enzymes, photons, or molecules that are not present under physiological conditions.

By "non-target molecule" is meant any molecule that is used for purposes of comparison with a target molecule in examining the reactivity of a reactive compound. An example of a non-target molecule is a free amino acid to which a reactive compound bonds; another example is a protein, other than the target protein, that contains the same amino acid in a solvent-accessible conformation.

By "protein-protein interaction" is meant contact between proteins that primarily involves polypeptide regions, rather than moieties such as sugars or lipids that are attached to the surface of a protein.

By "synthetic" is meant a compound or composition made by, e.g., recombinant techniques or synthetic organic techniques, rather than a compound isolated from a natural source.

By "substantially pure" is meant that a compound, such as a Bifunctional Blocker of the invention, has been separated from substances which naturally accompany it, or which are generated during its preparation or extraction. Such substances include organic solvents, reaction precursors, and other possible contaminants. Substances such as water, buffers, chemicals introduced to increase the stability of the compound, or chemicals added for formulation purposes are not considered contaminants. Preferably the compound is at least 80%, more preferably at least 95%, and most preferably at least 99%, by weight, free from other compounds, such as proteins, lipids, and other naturally-occurring molecules with which it is naturally associated. The purity of the compounds of the invention can be measured by any appropriate method, for example, gas chromatography analysis or high performance liquid chromatography analysis.

By a "disease" is meant a condition of a living organism which impairs normal functioning of the organism, or an organ or tissue thereof.

The present invention provides a number of advantages. For example, the compounds of the invention bind to a non-enzymatic protein or to a surface of an enzyme that is not part of its active site; a covalently bound portion of the compound sterically blocks the binding of that protein to another protein. These compounds contain two distinct chemical moieties: a Specificity Group (S group) that mediates non-covalent interactions with a target protein, and a Bonding Group (B group) that covalently bonds with an amino acid on the target protein. Modification of the S group has a relatively small effect on the bonding activity of the B group, and modification of the B group has a relatively small effect on the non-covalent binding affinity of the S group. As a result of these unique features, the compounds of the invention covalently bond to target proteins tightly enough to result in therapeutic utility, while at the same time bonding to non-target molecules in the body at a rate low enough to avoid drug allergies and other side effects that may result from non-specific interactions with non-target molecules. The methods of the invention provide an improvement over existing drug optimization techniques, in that they allow the independent optimization of distinct portions of compounds of the invention.

Other features and advantages of the invention will be apparent from the following detailed description thereof, and from the claims.

DETAILED DESCRIPTION

Figure 1D:
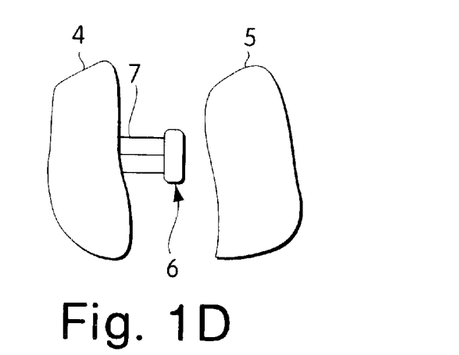
FIG. 1D is a schematic representation of a Bifunctional Blocker that is covalently bonded to a protein and that sterically blocks the binding of two proteins.

The invention features compounds, compositions, and methods for blocking protein-protein interactions. The compounds of the invention sterically hinder the interaction of a target protein with another protein by bonding to a surface of the target protein and by blocking protein-protein interaction. For example, as shown in FIG. 1D, the compound 6 is covalently bound to a protein 4 via a covalent bond 7. The compound 6 blocks the binding of a second protein 5 to the target protein 4. Preferred compounds bind to target proteins more tightly than the protein's normal binding partners bind. At the same time, the preferred compounds do not significantly bind to non-target molecules. As such, the compounds of the invention strike a balance between selectivity and reactivity.

Compounds that perform the above functions, referred to herein as Bifunctional Blockers or BB's, are molecules that contain a Specificity Group (S group) that mediates non-covalent affinity for the target protein, and a distinct Bonding Group (B group) that covalently bonds to the target protein. The S group may also determine the orientation of the B group relative to its target amino acid. The S group can be varied without significantly affecting the bonding reactivity of the B group, and the B group can be varied without significantly affecting the non-covalent binding affinity of the S group to the target protein.

Bifunctional Blockers are developed as follows. Lead compounds are initially identified by standard methods of medicinal chemistry, such as by rational drug design or by mass screening of chemical compound libraries in assays for drug activity. Alternatively, a lead compound may be constructed by the addition of a reactive group to a small-molecule drug that non-covalently binds to a target protein and sterically hinders the target protein's interaction with a second protein.

The lead compounds are then improved through a method called Bidirectional Optimization. By this method, the step of lead optimization of the S group is alternated with stepwise decreases in the covalent bonding reactivity of the B group. Lead optimization of the S group includes synthesizing chemical variants of the lead compound, testing the variants in the assays, and selecting compounds with improved activity and selectivity. Lead optimization often involves several cycles of improvement; it is common for each cycle to result in 2-fold to 50-fold improvements in affinity or selectivity for a given target. The concepts and methods of lead optimization are familiar to those skilled in the art of pharmaceutical development, and are documented in the medicinal chemistry literature.

The covalent bonding reactivity of the B group is modified by changing factors that control rates of covalent bond formation, which are known to those skilled in the art of organic chemistry. For example, the electronic influence of a substituent on the reactivity of a small molecule is described by the Hammett equation. The Hammett equation can therefore be used to predict how the reactivity of a small molecule will vary when a substituent, which does not form covalent bonds to a second reactant, is changed. Similarly, the effects of substituting a leaving group or introducing a sterically hindered group can be predicted, as described in Lowry and Richardson, *Mechanism and Theory in Organic Chemistry*, ch. 2, 4 (3d ed. 1987).

The S group and the B group can be linked with a spacer group, such as an alkyl chain, such that modification of the S group has little effect on the reactivity of the B group. For example, the phenyl ring of the substituent —$C_6H_4COOH$ can be seen as the S group, and the carboxyl group can be seen as the B group. Substituents on the S group affect the ionization constant of the B group in benzoic acid. The effect of the substituents on the S group, however, are significantly decreased in the substituent —$C_6H_4CH_2COOH$, which has a methylene group (the spacer group) between the S and the B group. The insertion of an even longer alkyl chain can further decrease the effect of substituents on the S group on the B group. This example illustrates one particular way in which the selectivity of the S group and the bonding reactivity of the B group may be relatively or completely independent of each other.

Figure 2A:
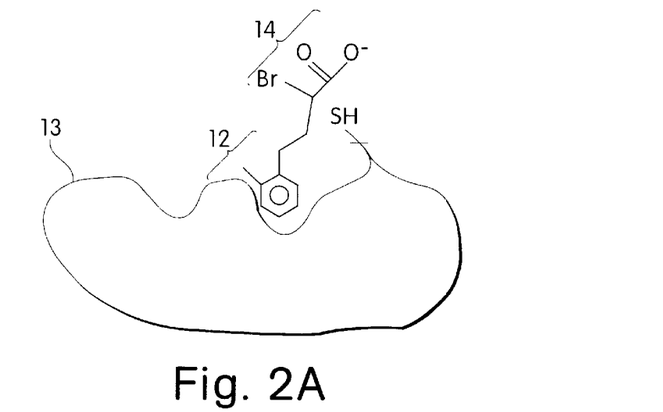
FIGS. 2A–2C are schematic representations of different Bifunctional Blockers bound to a hypothetical target protein.
Figure 2B:
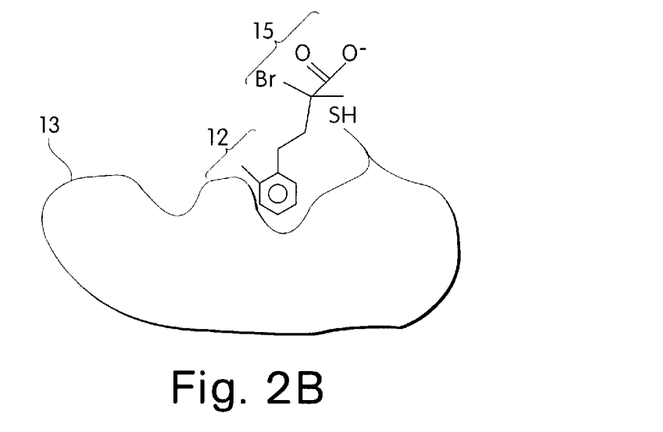
Figure 2C:
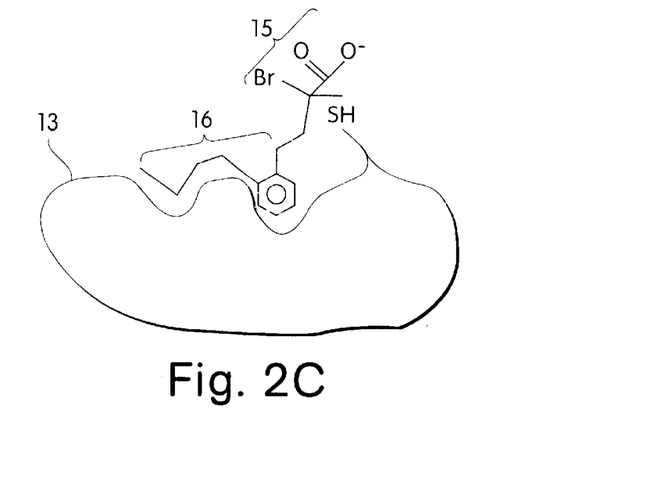

FIG. 2 illustrates a simple example of Bidirectional Optimization. FIG. 2A shows a non-optimized, highly reactive Bifunctional Blocker with an S group 12 that binds to a target protein 13 in such a way that the B group 14 is positioned to bond covalently with an amino acid side chain. FIG. 2B shows a Bifunctional Blocker with a B group 15 that is less reactive than the B group 14 shown in FIG. 2A; and FIG. 2C shows a Bifunctional Blocker that has an S group 16 that has a higher affinity for the target protein 13 than the S group 12 shown in FIG. 2A.

In its simplest form, Bidirectional Optimization proceeds as follows.

(1) A candidate compound is selected using procedures known in the art. For example, combinatorial chemistry can be used to generate large numbers of compounds that can then be screened for drug activity. The methods of, e.g., Hogan, *Nature Biotechnology* 15: 328–330 (1997); Janda et al., *Methods Enzymol.* 267:234–247 (1996); or Gordon, *Curr. Opin. Biotechnol.*6(6): 624–631 (1995) can be used. Alternatively, variations on the computer-based method of Li et al., *Proc. Nat. Acad. Sci.* 94: 73–78 (1997) can be used to identify an initial candidate compound with a desired activity.

The candidate compound is tested for its inhibitory activity (e.g., an $IC_{50}$ value) against the desired target protein in an assay, such as an in vivo or in vitro protein-protein binding assay. The compound is also tested for activity against non-target proteins or free amino acids in parallel assays. The assay of the non-target proteins can measure, for example, inhibition of protein-protein interaction or inhibition of cell growth.

The overall activity of the compound is determined by two parameters: the affinity of the S group for the target protein, and the reactivity of the B group with the side chain of an amino acid. These two parameters are altered in Bidirectional Optimization. However, because they cannot always be measured directly, these parameters are sometimes inferred from measurable quantities. The reactivity of the B group with the side chain of an amino acid can be measured directly; alternatively, it can be inferred by assaying the compound's effect on the interaction between non-target proteins containing this amino acid. The affinity of the S group for the target protein cannot be measured directly. Instead, what is measured is the ability of a given Bifunctional Blocker to inhibit the interaction between the target protein and a second protein. The overall activity of the Bifunctional Blocker is then inferred from this inhibiting activity. The affinity of the S group can in turn be inferred from the overall activity of the compound, and from the reactivity of the B group.

(2) Derivatives of the candidate compound selected in Step (1), in which the S group is varied but the B group remains unchanged, are then prepared. These derivatives are made by combinatorial chemistry techniques, by rational drug design methodologies, or by any other method of chemical design and synthesis familiar to those skilled in the art of pharmaceutical lead compound optimization. The derivatives are assayed against the target protein and non-target proteins as described in Step (1). Derivatives that exhibit increased activity against the target protein, and exhibit unchanged or decreased activity against the non-target proteins, are chosen for further development.

Figure 3A:
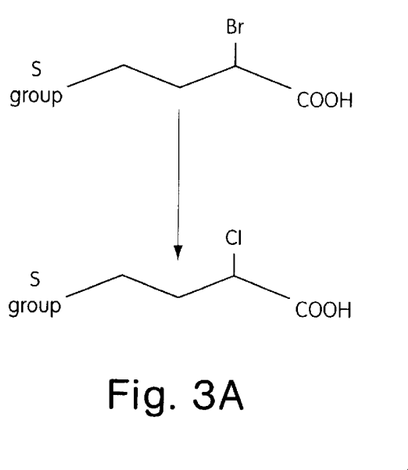
FIGS. 3A–3C are schematic representations of different ways in which to alter the reactivity of a compound to nucleophilic attack.
Figure 3B:
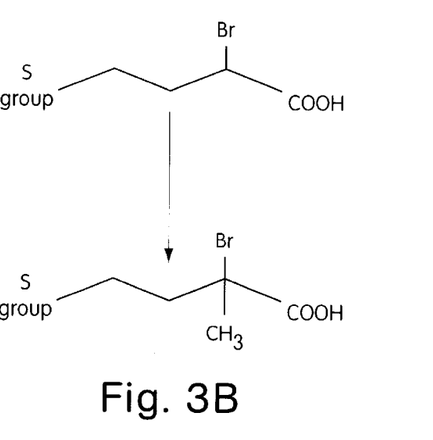
Figure 3C:
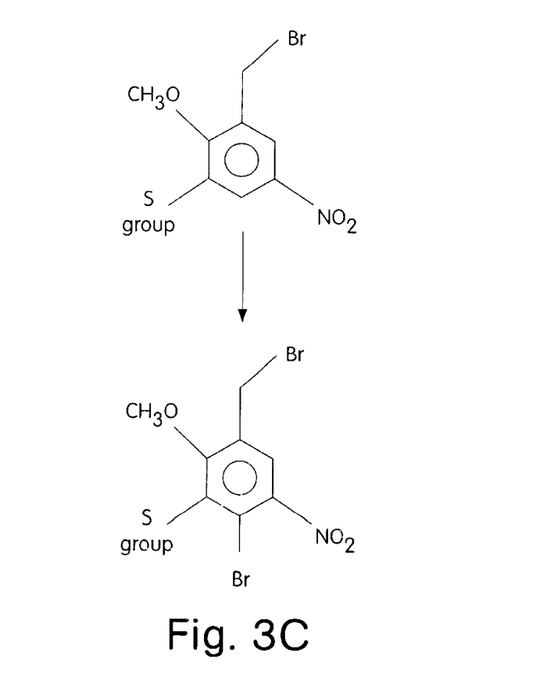

(3) The compounds selected in Step (2) are further modified by decreasing the reactivity of the Bonding Group. These decreases are made in accordance with well-established rules of chemical bond formation, as described in Lowry and Richardson, *Mechanism and Theory in Organic Chemistry*, ch. 2, 4 (3d ed. 1987). For example, the steps of changing the leaving group from Br to Cl (shown in FIG. 3A) or making the compound more sterically hindered (shown in FIG. 3B) each make a compound less reactive toward nucleophilic attack. In addition, adding an electron-withdrawing group (shown in FIG. 3C) or an electron donating group can make the compound less reactive toward nucleophilic attack.

Based on the documented reactivity of chemically reactive groups, the reactivity of the B group can be decreased in increments of 3-fold to 20-fold, or more. The inhibitory activity of the compound in both the target assay and the non-target assay is decreased by about the same amount. Compounds with decreased reactivity are then selected for further optimization.

When the B group is changed, the quantitative effect on reactivity can often be predicted with some precision. For this reason, it is often practical to change and decrease the reactivity of the B group at the same time that the S group is varied.

(4) The selected compounds from Step (3) are then subjected to further rounds of Bidirectional Optimization. The above steps need not be performed in strict alternation. For example, a round of alteration of the S group may not yield sufficient improvement; in this case, the S group is modified again before the B group is altered.

Bidirectional Optimization is continued until a compound is obtained that has the desired selectivity for the target protein and non-reactivity for non-target molecules.

The B group of a Bifunctional Blocker forms a covalent bond with a side chain of an amino acid on the target protein to form a stable product. A stable product has a sufficiently long half-life in physiological conditions that useful inhibition of the target protein results. Thus, the rate of reaction of the Bifunctional Blocker and the amino acid side chain of the target protein is not the important factor; the important issue is that the two react to give a stable product. For example, some amino acid side chains, such as cysteine, react quickly; these side chains, however, give relatively unstable products when reacted with B Groups such as esters, aldehydes, and ketones.

Bifunctional Blockers are able to bind selectively to target proteins because the S group brings the B group into close proximity with the target protein surface. The B group is thus physically constrained to be near the amino acid with which it reacts. The effective concentration of a physically constrained reactive group can be as high as $10^5$ to $10^7$ M in the neighborhood of its target group, leading to a significant enhancement of the reaction rate. This high effective concentration results from several factors, including physical proximity, loss of rotational entropy, and loss of translational entropy. The Bifunctional Blockers described in this application bring reactive groups into close physical proximity, and result in a loss of translational entropy. A conservative estimate is that a typical effective concentration of a reactive B group, when part of a protein-bound Bifunctional Blocker, is about $10^3$ M.

In addition to being selective for the target protein, the Bifunctional Blocker must be sufficiently non-reactive with non-target molecules that significant adverse side effects, such as drug allergy, do not result. The desired level of reactivity can be determined using, as a model, a compound known to occasionally cause drug allergy. One particular example of such a compound is penicillin, which is well-known to cause allergic symptoms in some patients. Penicillin modifies blood proteins non-specifically by covalently bonding to lysine, and, as a result, certain individuals in a population suffer an allergic reaction to this drug. The vast majority of the population, however, does not have such an allergic response. The forward reaction rate of penicillin with lysine side chains in proteins, which is about $1\times10^{-5}$/M/sec in physiological conditions, can therefore be considered an approximate upper limit for a safe level of reactivity with a non-target protein.

In sum, using the technique of Bidirectional Optimization, Bifunctional Blockers that bind tightly to target proteins, yet are sufficiently unreactive with non-target molecules to avoid side effects such as drug allergy, may be synthesized. These compounds can be formulated into pharmaceutical compositions using techniques known to those skilled in the art.

There now follow particular examples of Bifunctional Blockers and Bidirectional Optimization according to the invention. These examples are provided for the purpose of illustrating the invention, and should not be construed as limiting.

EXAMPLE 1

Inhibition of the Fos/Jun Interaction

Fos and Jun are inducible DNA-binding proteins that turn on transcription as a final step in many different signal transduction pathways. For example, the transcription of Fos is activated when Nerve Growth Factor is added to PC12 cells. Nerve Growth Factor is a stimulator of pain sensation in adult mammals; blocking Fos function is therefore a useful approach to the treatment of chronic pain. Fos has a cysteine thiol group, which reacts with alkyl halides on or near its surface of interaction with Jun; covalent attachment of a typical drug-sized molecule to this group would therefore disrupt Fos/Jun interactions.

A Bifunctional Blocker for this purpose is developed as follows. A family of candidate compounds is synthesized by combinatorial chemistry using, for example, the method of Hogan, *Nature Biotechnology* 15:328–330 (1997); Janda et al., *Methods Enzymol.* 267:234–247 (1996); or Gordon, *Curr. Opin. Biotechnol.* 6(6): 624–631 (1995) to generate S groups. The B group of these compounds is preferably an alpha-bromo carboxylic acid, which is expected to undergo nucleophilic attack by the cysteine thiol group with a forward rate constant of about $8\times10^{-5}$/M/sec. A B group is attached to each of the S groups of the compounds by a straight alkyl chain of any appropriate length. An example of such a compound is [S group]—$CH_2CH_2CH_2CHBrCOOH$.

The activity of each candidate compound is assayed, for example, as follows. Fos is bound to the bottom of a microtiter plate by standard procedures. Each candidate compound is added to a final concentration of 1 $\mu$M and incubated with the Fos protein for 45 minutes. The plate wells are washed to remove unbound compounds. Fluoresceinated Jun protein and a DNA oligonucleotide comprising a Fos/Jun binding site are then added. The mixture is incubated for an additional 30 minutes; the wells are washed, and the binding of fluoresceinated Jun is measured. Compounds that cause at least 90% inhibition are examined for further study. Alternatively, a variation of the gel-shift assay used by Abate et al., *Science* 249: 1157–1161 (1990), or a variation of the assay for protein-protein interaction of Devos et al., *European Journal of Biochemistry* 225: 635–640 (1994), may be used to assay Fos/Jun interactions.

For a provided candidate compound, the affinity of the S group for Fos can be expected to be $K_{affinity}=10^4$/M. When the compound is non-covalently bound to a protein, the effective concentration of its B group in the range of the target cysteine is likely to be at least $10^3$ M. (Although in practice, the affinity of the S group and the effective concentration of the B group are often not determinable as separate quantities.) The fractional occupancy is the extent to which the compound, present in excess and under non-saturating conditions (i.e., at a concentration of $10^{-6}$ M), non-covalently binds to the target protein, and is given by the following equation:

$$\text{fractional occupancy}=[\text{concentration of Blocker}]\times K_{affinity}=10^{-6}\text{M}\times 10^4/\text{M}$$

Under these circumstances, the forward rate (k) of covalent bonding is $$(\text{fractional occupancy})\times(\text{effective concentration with full occupancy})\times(\text{forward rate constant for compound with free cysteine})\times[\text{protein concentration}]=0.01\times1000\text{ M}\times0.0001/\text{M/sec}\times[\text{protein conc.}]=10^{-3}/\text{sec}\times[\text{protein concentration}].$$

The proportion of unreacted protein that remains after time t is given by ($e^{-kt}$), where k is the forward rate of covalent bonding and t is time in seconds. It follows that the amount of covalently bonded protein is ($1-e^{-kt}$). Thus, the rate calculated using the above equation indicates that, in 45 minutes (2700 seconds), the provided candidate compound covalently bonds to ($1-e^{-2.7}$), or 95%, of the target protein, and causes a 95% inhibition in the protein interaction assay described above.

The —$CH_2CH_2CH_2CHBrCOOH$ B group is replaced with a —$CH_2CH_2CH_2C(CH_3)BrCOOH$ B group, which is expected to be about 15-fold less reactive. At the same time, derivatives of the S group are attached to the new B group. The new compounds are assayed as described above. Due to the decreased reactivity of the new B group, the S group must be able to bind at least 7-fold more tightly than the previous S group to achieve 90% inhibition in the assay. If an improvement of less than 7-fold in the binding constant of the S group is achieved, less than 90% inhibition will be achieved. In this case, further modifications of the S group are made before the B group is altered again.

In the second round of Bidirectional Optimization, the —$CH_2CH_2CH_2C(CH_3)BrCOOH$ B group is replaced with a —$CH_2CH_2CH_2CHClCOOH$ B group, which is expected to be about 15-fold less reactive than the —$CH_2CH_2CH_2C(CH_3)BrCOOH$ B group. At the same time, derivatives of the S group are synthesized and attached to the —$CH_2CH_2CH_2CHClCOOH$ B group. The compounds are assayed as described above.

A compound containing an S group that, in combination with the —$CH_2CH_2CH_2CHClCOOH$ B group, causes the same inhibition of Fos-Jun interaction, represents about a 200-fold improvement in the Bifunctional Blocker. This improved compound has about the same reactivity for the target protein as the starting compound, but the selectivity of the compound is improved by about 200-fold.

A Bifunctional Blocker with a —$CH_2CH_2CH_2CHClCOOH$ B group has a non-specific covalent bonding rate with proteins of about $4\times10^{-7}$/M/sec, which is significantly lower than the covalent bonding rate for penicillin; this compound is therefore potentially useful as a drug.

EXAMPLE 2

Inhibition of the IL-1/IL-1R Interaction

The IL-1 beta protein interacts with the IL-1 receptor (IL-1R) to stimulate inflammation. Disruption of this process is therefore a useful approach for treating a number of inflammatory diseases. There is a solvent-exposed methionine residue (Met36) in IL-1 beta near its interaction surface with IL-1R, and attachment of a drug-sized molecule to this residue is expected to disrupt the interaction with IL-1R.

Figure 4:
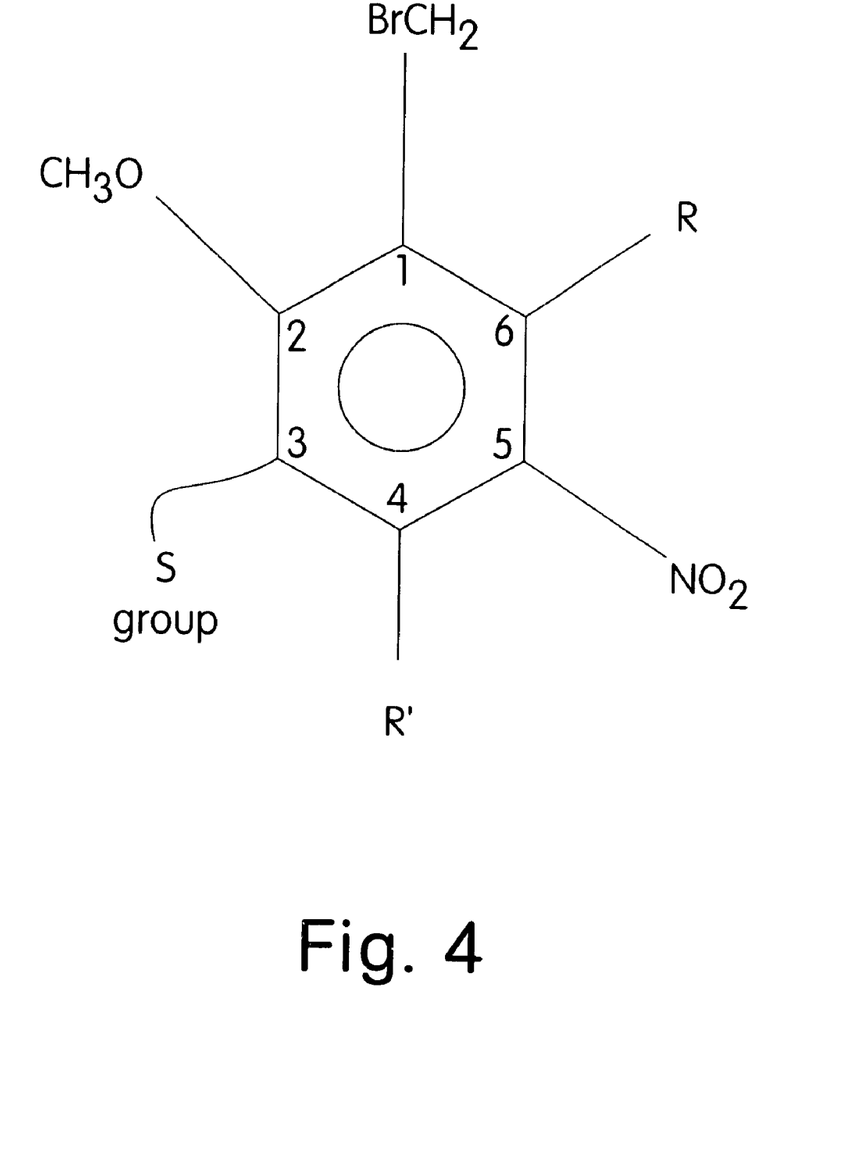
FIG. 4 is a schematic representation of a compound that includes an S group and a B group.

In this particular example, a provided compound with a B group consisting of 2-methoxy-5-nitrobenzyl bromide, shown in FIG. 4, is preferably used as the starting point. 2-Methoxy-5-nitrobenzyl bromide covalently bonds to tryptophan, methionine, and cysteine residues in proteins. The rate of reaction with methionine and tryptophan is similar, and is about $1.5–3\times10^{-3}$/M/sec. The reaction occurs by an $S_N1$ mechanism; the reaction rate is therefore relatively insensitive to the reactivity of the nucleophilic amino acid, and instead depends on the reactivity of the electrophile. The reactivity of 2-methoxy-5-nitrobenzyl bromide is strongly influenced by the electronic effects of substituents on the benzene ring. The addition of electron-withdrawing groups, such as halides, decreases the rate of $S_N1$ reactions.

To illustrate the power of the Bidirectional Optimization method, a candidate compound including an S group having a non-covalent affinity of only $K_{affinity}=10^3$/M for IL-1 beta is used in this example. The reactivity of the candidate compound including 2-methoxy-5-nitrobenzyl bromide will be about the same as the reactivity of 2-methoxy-5-nitrobenzyl bromide itself, because the electronic effect of the S group is small. Therefore, the candidate compound has a non-specific reaction rate with exposed methionine side chains of about $1\times10^{-3}$/M/sec.

The interaction of IL-1 beta with the soluble form of IL-1R is assayed in a protein-based assay similar to those described above, using the same protein concentrations and incubation times as described above.

When the compound is non-covalently bound to IL-1 beta, there is likely to be an effective concentration of at least $10^3$ M of the 2-methoxy-5-nitrobenzyl bromide group in the neighborhood of Met36. In this example, the fractional occupancy is $10^{-6}M\times10^3/M$ 0.001. According to the equation of Example 1, the forward rate of production of covalently bonded protein is $10^{-3}\times$[protein concentration].

Bidirectional Optimization is used to reduce the non-specific reactivity of the compound to equal to or less than that of penicillin as follows. The 2-methoxy-5-nitrobenzyl bromide group is replaced by a similar group with a fluorine in the 6 (ortho) position; this replacement reduces reactivity by about 20-fold. At the same time, variants of the S group are attached to this new, less reactive B group, and the new compounds are screened for activity. The compounds that are most effective in blocking the IL-1 beta/IL-1R interaction are chosen for further optimization. These compounds are also checked for reduced reactivity with free methionine and with non-target molecules.

A second step of Bidirectional Optimization proceeds as follows. The 2-methoxy-5-nitro-6-fluorobenzyl bromide B group is replaced with 2-methoxy-5-nitro-6-bromobenzyl bromide; this replacement depresses the reaction rate even further. As described above, the S group is further modified. The most active compounds are then tested for reduced reactivity against free methionine and against non-target proteins.

An alternative way to use Bidirectional Optimization to reduce the non-specific reactivity of the compound to equal to or less than that of penicillin is to introduce a bromine at the 4 position of the benzene ring (an ~5-fold effect), or to replace the bromine leaving group with a chlorine (an ~40-fold effect). These effects are summarized in Tables 1 and 2. The non-specific reactivity of the compound will then be less than $10^{-5}$/M/sec, which is comparable to the reactivity of penicillin for amino acid side chains in proteins.

TABLE 1

Effects of halogen substitutions of the phenyl ring on $S_N1$ reaction rates.

| | Relative reaction rate |
|---|---|
| R = H | 1.0 |
| R = F | 0.05 |
| R = Br | 0.006 |
| R' = H | 1.0 |
| R' = Br | 0.2 |

TABLE 2

Effects of the leaving group on $S_N1$ reaction rates.

| Leaving group | Relative reaction rate |
|---|---|
| Br | 1 |
| Cl | 0.025 |

EXAMPLE 3

Inhibition of the MCP-1/CCR2 Interaction

Monocyte/Macrophage Chemotactic Protein-1 (MCP-1), a chemokine released by inflamed cells, attracts monocytes and macrophages to sites of tissue damage. Its receptor, CC-Chemokine Receptor 2 (CCR2), is present on the surface of monocytes and macrophages. Both of these proteins are thought to play a role in the development of atherosclerosis. Atherosclerosis develops when macrophages migrate into the subendothelial space in a blood vessel, take up cholesterol, and turn into "foam cells," which then die and leave behind cholesterol crystals. The inhibition of the interaction of MCP-1 and CCR2 is therefore potentially useful for controlling atherosclerosis and other inflammatory diseases.

The three-dimensional structure of MCP-1 has been determined. It is thought that amino acids 22 to 34 play a key role in the interaction between MCP-1 and CCR2. Possible targets for covalent modification include Lys44, which is adjacent to the stretch of amino acids 22 to 34, Ser27, and Ser34.

A Bifunctional Blocker that binds to MCP-1, thereby disrupting its interaction with CCR2, is developed as follows. A compound that is known to bind non-covalently to the MCP-1 pocket, such as a peptide segment from CCR2, is used as a Specificity Group. Alternatively, an S group is chosen using conventional screens that identify compounds that inhibit the MCP-1/CCR2 interaction. In one particular example, the provided compound has an S Group with a predicted non-covalent affinity for MCP-1 of $K_{affinity}=10^3$/M ($K_{dissociation}$=1 mM.

A Bonding Group, such as the aspirin derivative 3,5-dibromoacetylsalicylic acid, is linked to the Specificity Group to construct a first-generation Bifunctional Blocker that covalently bonds to MCP-1. The B Group is attached to the S Group by an alkyl chain of any length. For example, an alkyl chain having between 2 and 12 carbon atoms may be used. An example of such a compound is 4-[S group]-3,5-dibromoacetylsalicylic acid. Such a compound has a reactivity with free lysine side chains of about $1 \times 10^{-3}$/M/sec, at 37° C., pH 7.5.

The candidate Bifunctional Blocker is incubated, at a concentration of 1 μM, for 45 minutes at 37° C. at pH 7.5 with purified $^{125}$I-labeled MCP-1. The inhibition of MCP-1 activity is assayed, for example, according to the procedure of Ernst et al. (*J. Immunol.* 152:3541–3549 (1994)). In this procedure, $^{125}$I-labeled MCP-1 is added to elutriated monocytes, which express the CCR2 receptor in their plasma membranes. Alternatively, an extract of the monocyte cell membranes is made and adhered to microtiter wells, according to standard procedures.

When the compound is non-covalently bound to MCP-1, the effective concentration of its B group in the range of a target lysine is calculated to be at least $10^3$ M. The fractional occupancy of the Bifunctional Blocker on MCP-1 is given by the following equation:

Fractional occupancy=concentration of Blocker×$K_{affinity}$= $10^{-6}$ M×$10^3$/M. Under these circumstances, the forward rate (k) of covalent bonding is (fractional occupancy)×(effective concentration with full occupancy)×(forward rate constant for compound with free lysine)×[protein concentration]= 0.001×1000 M×0.001/M/sec×[protein concentration]=$10^{-3}$/sec×[protein concentration].

The proportion of unreacted protein that remains after time t is given by ($e^{-kt}$), where k is the forward rate of covalent bonding and t is the time in seconds. Thus, the rate calculated using the above equation indicates that, in 45 minutes (2700 seconds), such a compound covalently bonds to (1-$e^{-kt}$), or 95%, of the target protein, and causes a 95% inhibition in the protein interaction assay described above.

The 3,5-dibromoacetylsalicylic acid B group is replaced with an acetylsalicylic acid (aspirin) B group, which is expected to be approximately 8-fold less reactive. At the same time, derivatives of the S group, generated by standard medicinal chemistry techniques, are attached to the new B group. The new compounds are assayed as described above. Because of the decreased reactivity of the new B group, the S group must be able to bind at least about 4-fold more tightly to achieve 90% inhibition in the assay. If an improvement of less than 4-fold in the binding constant of the S group is achieved, less than 90% inhibition will be achieved. In this case, further modifications of the S group are made before the B group is altered again.

A compound containing a S group that, in combination with the acetylsalicylic acid B group, is an effective inhibitor of MCP-1/CCR-2 interaction. At the same time, this Bifunctional Blocker has approximately the non-specific reactivity of aspirin, a compound that has been shown to be quite safe.

The use of acylating agents such as aspirin, penicillin, and their derivatives helps avoid the modification of important cysteine-containing non-target proteins. Cysteine is the most reactive of all the amino acid side chains. Because the side chain of cysteine has a much more reactive nucleophile than, for example, the side chain of lysine or serine, cysteines on important proteins can become substantially modified. When these cysteines are altered, the corresponding proteins become inhibited, resulting in undesired side effects. When aspirin is used as an acylating agent, however, the acylation of cysteine results in an unstable thiol ester that spontaneously hydrolyzes to regenerate cysteine. The cysteine-containing proteins therefore remain substantially unaltered.

EXAMPLE 4

Preparation of Combinatorial Chemistry Libraries

Libraries of compounds may be synthesized using combinatorial chemistry techniques, in which a particular B group is incorporated into each member of the library. For convenience, a Bonding Group with a reactivity about the same as that of penicillin is preferably employed.

The strategies and techniques for generating such combinatorial libraries are familiar to those skilled in the art of medicinal chemistry. To incorporate a reactive Bonding Group into the library, it is necessary to add the reactive Bonding Group in a protected form, to add the Bonding Group in the final synthetic step, or to take some other precaution to ensure that the Bonding Group does not undergo a reaction during construction of the library. The specific strategies and techniques to accomplish such a synthesis are familiar to those skilled in the art of medicinal chemistry.

All publications and patents mentioned in this specification are herein incorporated by reference to the same extent as if each individual publication or patent was specifically and individually indicated to be incorporated by reference.

Other Embodiments

From the foregoing description, it will be apparent that variations and modifications may be made to the invention described herein to adopt it to various usages and conditions. Such embodiments are also within the scope of the following claims.

What is claimed is:

1. A method of producing a compound that selectively binds to a target protein and sterically blocks binding of said target protein to a second protein, said method comprising:

(a) providing a candidate compound having a molecular weight of less than 1500 daltons and comprising a Specificity Group and a Bonding Group, wherein said Bonding Group covalently bonds to an amino acid side chain of said target protein and said Specificity Group does not covalently bond to any amino acid side chain;

(b) testing said candidate compound for its level of inhibition of the interaction of said target protein with said second protein;

(c) testing said candidate compound for its level of binding to a non-target molecule;

(d) altering said Specificity Group and selecting for increased selectivity for said target protein relative to that measured in steps (b) and (c), wherein increased selectivity is indicated by an increase in the inhibition of the interaction of said target protein and said second protein, relative to said binding to said non-target molecule;

(e) replacing said Bonding Group with a group known to be less reactive with said amino acid side chain of said target protein, altering the Specificity Group of step (d), and selecting for substantially unchanged or increased inhibition relative to said inhibition of said interaction measured in step (d); and (f) optionally repeating steps (d) and (e), whereby a compound is obtained that has a selectivity for the target protein, relative to the non-target molecule, that is at least 100 times greater than said candidate compound of step (a).

2. The method of claim 1, wherein said compound selectively binds to said target protein at an amino acid side chain that is not part of an enzyme active site, and wherein said compound binds to said target protein at a site of interaction between said target protein and said second protein.

3. The method of claim 1, wherein said target protein is not an enzyme.

4. The method of claim 1, wherein said compound is a synthetic compound.

5. The method of claim 1, wherein said Specificity Group and said Bonding Group are connected by an alkyl chain of between 2–12 carbons.

6. The method of claim 1, wherein said Bonding Group is an alkyl halide.

7. The method of claim 1, wherein said Bonding Group is a benzyl compound.

8. The method of claim 1, wherein said Bonding Group is an acylating agent.

9. The method of claim 1, wherein said Bonding Group reacts with a sulfur, nitrogen, or oxygen of said amino acid side chain of said target protein.

10. The method of claim 1, wherein said Bonding Group reacts with a cysteine, methionine, tryptophan, lysine, or serine amino acid of said target protein.

11. The method of claim 1, wherein said amino acid is a nucleophile.

* * * * *

UNITED STATES PATENT AND TRADEMARK OFFICE
CERTIFICATE OF CORRECTION

PATENT NO. : 6,465,192 B2
DATED : October 15, 2002
INVENTOR(S) : Jeffrey C. Way

It is certified that error appears in the above-identified patent and that said Letters Patent is hereby corrected as shown below:

Title page,
Item [56], References Cited, OTHER PUBLICATIONS, add -- Birnbaum and Mosbach, "Peptide Screening," *Current Opinion in Biotechnology* 3: 49-54 (1992). --

Column 1,
Line 26, "binds to especially" should be -- binds especially --.

Signed and Sealed this

Fourth Day of January, 2005

JON W. DUDAS
*Director of the United States Patent and Trademark Office*